United States Patent [19]

Distelmans et al.

[11] Patent Number: 5,236,944
[45] Date of Patent: Aug. 17, 1993

[54] COMPOUNDS, COMPOSITIONS AND ANTI-NEOPLASTIC METHODS

[75] Inventors: Willem H. K. M. Distelmans, Berchem; Jan Heeres, Vosselaar; Robert F. Van Ginckel, Vorselaar, all of Belgium

[73] Assignee: Janssen Pharmaceutica N.V., Beerse, Belgium

[21] Appl. No.: 977,733

[22] Filed: Nov. 16, 1992

Related U.S. Application Data

[63] Continuation of Ser. No. 630,426, Dec. 19, 1990, abandoned, which is a continuation of Ser. No. 321,429, Mar. 9, 1989, abandoned.

[30] Foreign Application Priority Data

Mar. 28, 1988 [GB]  United Kingdom ................. 8807314
Dec. 22, 1988 [GB]  United Kingdom ................. 8829966

[51] Int. Cl.$^5$ .................. A61K 31/415; C07D 405/06
[52] U.S. Cl. ..................................... 514/397; 514/58; 548/311.1
[58] Field of Search ................. 548/311.1; 514/58, 397

[56] References Cited

U.S. PATENT DOCUMENTS

4,490,540  12/1984  Heeres et al. ........................ 548/336
4,764,604   8/1988  Muller ................................. 536/103

FOREIGN PATENT DOCUMENTS

149197  7/1985  European Pat. Off. .

OTHER PUBLICATIONS

R. Van Ginckel, et al., *Anticancer Research* 6:705–708 (1986).
W. Distelmans, et al., *Invasion and Metastasis* 5:170–184 (1985).
R. Van Ginckel, et al., *Eur. J. Cancer Clin. Oncol.* 20:99–105 (1984).
G. Gevens, et al., *Cancer Research* 45:733–742 (1985).

*Primary Examiner*—Joseph Paul Brust
*Assistant Examiner*—Jacqueline Haley
*Attorney, Agent, or Firm*—Charles J. Metz

[57] ABSTRACT

Method of treating neoplasms hosting in mammals by administering a $C_{1-4}$alkyl [4-[2-(4-$C_{1-4}$alkylphenyl)-2-(1H-imidazol-1-ylmethyl)-1,3-dioxolan-4-ylmethyl-thio]phenyl]carbamate. Pharmaceutical compositions containing the same as active ingredient. Compounds used in said method and process for preparing said compounds.

18 Claims, No Drawings

COMPOUNDS, COMPOSITIONS AND ANTI-NEOPLASTIC METHODS

CROSS-REFERENCE TO RELATED APPLICATIONS

This application is a continuation of application Ser. No. 630,426, filed on Dec. 19, 1990, now abandoned, which was a continuation of application Ser. No. 321,429, filed on Mar. 9, 1989, now abandoned.

BACKGROUND OF THE INVENTION

Up until now there are described a number of antineoplastic drugs which interfere with the structure and function of microtubules in both interphase and mitotic cells. As most important compounds having said properties their may be named nocodazole, vinblastine, vincristine sulfate and cis-ethyl[4-[2-(2,4-dichlorophenyl)-2-(1H-imidazol-1-ylmethyl)-1,3 -dioxolan-4-ylmethylthio]phenyl]carbamate, generically designated as tubulozole. The latter is described among other structurally similar compounds in U.S. Pat. No. 4,490,540 and is specifically described in Cancer research 45, 733–742 (1985), Invasion and Metastasis 5, 170–184 (1985) and Eur. J. Cancer Clin. Oncol. 1, 99–105 (1984) as a microtuble inhibitor useful in the treatment of neoplasms. The present $C_{1-4}$alkyl[4-[2-(4-$C_{1-4}$alkyloxyphenyl) -2(1H-imidazol-1-ylmethyl)-1,3-dioxolan-4-ylmethylthio]phenyl]carbamates differ from the known compounds by their alkyloxy substitution on the phenyl ring and specifically by their favourable antineoplastic properties.

DESCRIPTION OF THE INVENTION

The present invention is concerned with a group of compounds particularly useful for treating mammals hosting a neoplasm, said compounds being represented by the formula

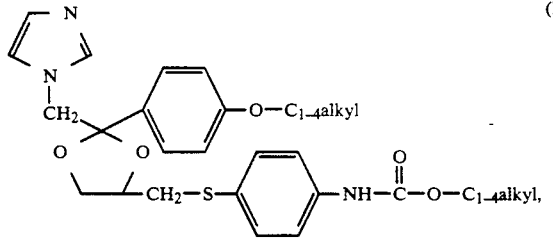

(I)

an acid addition or a stereochemically isomeric form thereof.

The preferred compounds of the present invention are those compounds of formula (I) wherein the substituents on the dioxolane moiety have a cis configuration.

The most preferred compounds of the present invention are selected from the group consisting of ethyl cis-[4-[[2-(1H-imidazol-1-ylmethyl)-2-(4-methoxyphenyl)-1,3-dioxolan-4-yl]methylthio]carbamate and the pharmaceutically acceptable acid addition salts thereof.

In the foregoing definitions $C_{1-4}$alkyl is meant to include straight and branch chained saturated hydrocarbon radicals having from 1 to 4 carbon atoms such as, for example, methyl, ethyl, propyl, 1-methylethyl, butyl, 1-methylpropyl, 2-methylpropyl, and 1,1-dimethylethyl, with methyl and ethyl being preferred.

The compounds of formula (I) can be used as such or in their acid-addition salt form, preferably a pharmaceutically acceptable acid addition salt form. The latter can conveniently be obtained by treating the base-form with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxy-butanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term acid addition salt as used hereinabove also comprises the solvates which the compounds of formula (I) are able to form and said solvates are meant to be included within the scope of the present invention. Examples of such solvates are e.g., the hydrates, alcoholates and the like.

The compounds of formula (I) can generally be prepared by S-alkylating an appropriately substituted benzenethiol of formula (III) with an alkylating reagent of formula (II).

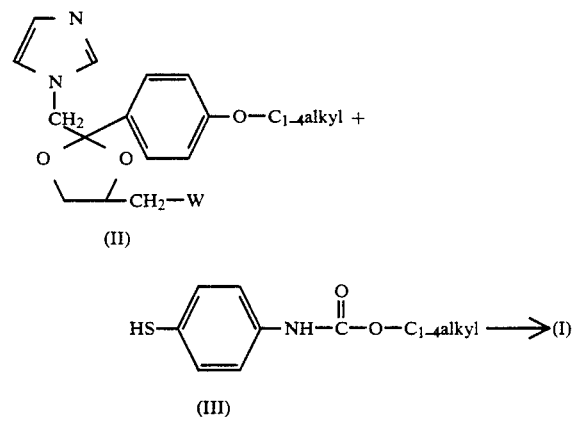

In formula (II) and in a number of the following intermediates, W represents a reactive leaving group such as, for example, halo, preferably chloro, bromo or iodo, or a sulfonyloxy groups such as, for example, methanesulfonyloxy, trifluoromethanesulfonyloxy, 2-naphthalenesulfonyloxy or 4-methylbenzenesulfonyloxy and the like reactive groups.

The alkylation reaction of (II) with (III) can be carried out under art-known conditions of performing S-alkylations. Said S-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester e.g. ethylacetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3,-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo[2,2,2]octane, pyridine and the like, may optionally be used to pick up the acid which is formed during the course of the reaction. Further, it may be advantageous to convert the intermediate of formula (III) first into a suitable salt form thereof such as, for example, an alkali or earth alkaline metal salt, by reacting (III) with an appropriate base as defined hereinabove and subsequently using said salt form in the reaction with the alkylating reagent of formula (II). Stirring and somewhat elevated temperatures of from about 30 to about 220° C., preferably form about 80 to about 170° C. may enhance the rate of the reaction; more in particular the reaction may be conducted at the reflux temperature of the reaction mixture. Additionally, it may be advantageous to conduct said S-alkylation under an inert atmosphere such as, for example, oxygen-free argon or nitrogen gas. Alternatively, said S-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethyl ammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

The compounds of formula (I) may alternatively be synthesized by N-alkylating an 1H-imidazole (IV) with an intermediate of formula (V).

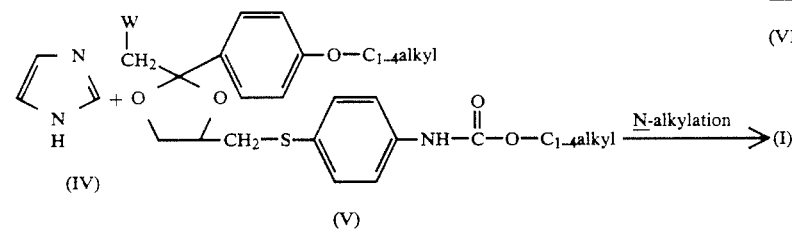

Said N-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethylacetate, γ-butyrolactone and the like; an ether, e.g. 1,1'-oxybisethane, tetrahydrofuran, 1,4-dioxane and the like a dipolar aprotic solvent, e.g. N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, 1H-imidazole, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. Further, it may be advantageous to convert the 1H-imidazole (IV) first into a suitable salt form thereof such as, for example, an alkali or earth alkaline metal salt, by reacting (IV) with an appropriate base as defined hereinabove and subsequently using said salt form in the reaction with the alkylating reagent of formula (V). In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation under an inert atmosphere such as, for example, oxygen-free argon or nitrogen gas.

Alternatively, said N-alkylation may be carried out by applying art-known conditions of phase transfer catalysis reactions as described hereinabove.

Alternatively, the compounds of formula (I) may be prepared by the acetalization reaction of a ketone of formula (VI) with a diol of formula (VII) in the presence of an acid such as, for example, benzenesulfonic acid, 4-methylbenzenesulfonic acid and the like acids.

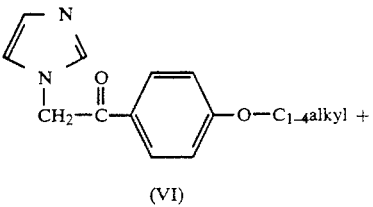

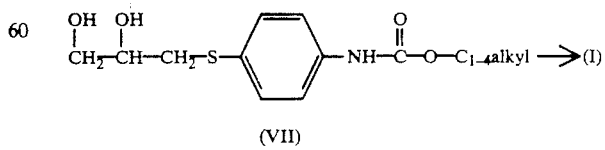

Said acetalization reaction may conveniently be conducted in a reaction inert solvent such as, for example, an aromatic hydrocarbon, e.g., benzene, methylbenzene, a halogenated hydrocarbon, e.g., trichloromethane, an alkanol, e.g., ethanol, butanol, propanol and the like, or a mixture of such solvents. Preferably, the water which is liberated during the course of the reaction, is removed by azeotropical destillation.

The compounds of formula (I) may also be obtained by reacting a benzeneamine of formula (VIII) with an appropriate reagent of formula (IX).

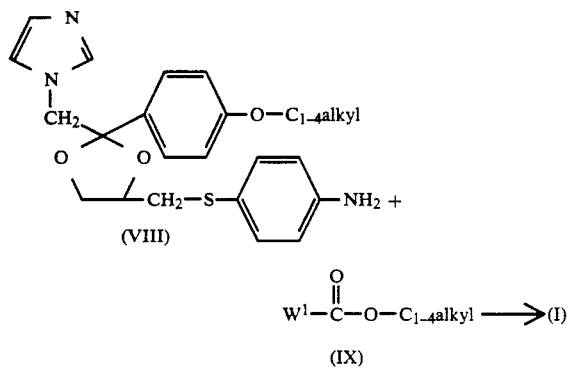

In (IX) $W^1$ represents a reactive leaving group such as, for example, halo, preferably chloro, $C_{1-6}$alkyloxy, aryloxy, aryl$C_{1-6}$alkyloxy or a $C_{1-4}$alkyloxycarbonyloxy group. Said reaction of (VIII) with (IX) may be carried out by stirring the reactants, preferably at somewhat elevated temperatures, in an appropriate organic solvent such as, for example, an aromatic hydrocarbon, e.g., benzene and methylbenzene; a halogenated hydrocarbon, e.g. dichloromethane and trichloromethane; pyridine; or a mixture of such solvents, in the presence of an appropriate base such as, for example, an alkali or earth alkaline metal carbonate, hydrogen carbonate or hydroxide, e.g., potassium carbonate, sodium hydrogen carbonate, potassium hydroxide and the like. In some cases it may be advantageous to carry out the reaction in a two-phase system, formed by water and a water-immiscible inert organic solvent.

Or, the compounds of formula (I) may be obtained by the addition-reaction of an appropriately substituted isocyanatobenzene of formula (X) with an alcohol of formula (XI).

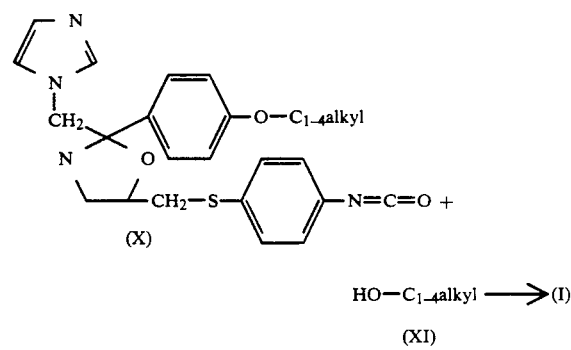

The addition of (X) with (XI) can generally be carried out by stirring and, if desired, heating the reactants together in a suitable solvent, such as, for example, water, acetic acid, a halogenated hydrocarbon, e.g., dichloromethane and the like, acyclic ether, e.g., 1,4-dioxane and the like. In some cases it may be advantageous to convert the alcohol (XI) first into a suitable salt form thereof such as, for example, a metal salt, be reacting (XI) with an appropriate base and subsequently using said salt form in reaction with (X).

From formula (I) it is evident that the compounds of this invention have at least two asymmetric carbon atoms in their structures, namely those located in the 2- and 4-position of the dioxolane nucleus. Consequently the compounds of formula (I) can exist under different stereochemically isomeric forms.

The diastereomeric racemates of (I), denoted as cis and trans forms according to the rules described in J. Org. Chem. 35 (9), 2849–2867 (1970), may be obtained separately by conventional methods. Appropriate methods which may advantageously be employed include, for example, selective crystallization and chromatographical separation, e.g., column chromatography.

Since the stereochemical configuration is already fixed in a number of intermediate compounds, e.g., in the intermediates of formulae (II), (V), (VIII) and (X), it is also possible to separate cis and trans forms at this or, when possible, even an earlier stage. Preferably the cis and trans forms are separated starting from cis/trans (1$\overline{H}$-imidazol-1-ylmethyl)-2 -(4-$C_{1-4}$alkyloxyphenyl)-1,3-dioxolane-4-methanol. The corresponding diastereomeric forms of (I) may be derived therefrom in the previously indicated manner. The separation of cis and trans forms of such intermediates may be performed by conventional methods as mentioned hereinabove for the separation of the cis and trans forms of the compounds of formula (I).

It is evident that the cis and trans racemates may be further resolved into their optical isomers, cis(+) and cis(−), respectively trans(+) and trans(−) by the application of methodologies known to those skilled in the art. In case additional asymmetric centra are present in the abovementioned intermediates and/or compounds, the resulting mixtures of stereoisomers may be further separated by the previously indicated methodologies. Preferably, if a specific stereochemical form is desired, said compound will be synthesized by stereoselective methods of preparation, which will advantageously employ enantiomerically pure starting materials.

A number of intermediates and starting materials used in the foregoing preparations are known compounds, others may be prepared according to art-known methodologies of preparing said or similar compounds, while still others are new. In general, the intermediates (II), (V), (VI), (VIII) and (X) used as starting materials, can be prepared following procedures analogous to those described in U.S. Pat. No. 4,490,540, and U.S. Pat. No. 4,101,666 incorporated herein by reference.

Starting materials of formula (II) may be derived from a 1-(4-$C_{1-4}$alkyloxyphenyl)-2-haloethanone by reacting the latter with an 1$\overline{H}$-imidazole in a reaction inert solvent, if appropriate in the presence of a base, and subsequently reacting the thus obtained 1-(4-$C_{1-4}$alkyloxyphenyl-2-(1$\overline{H}$-imidazol-1-yl)ethanone (VI) with 1,2,3-propanetriol in a suitable acetalizing medium. The desired alkylating reagents of formula (II) can easily be prepared by converting the remaining hydroxy group of the obtained intermediate into a reactive leaving group according to methodologies generally known in the art. Said reactive derivatives of formula (II) can alternatively be prepared according to a sequence of reactions similar to the procedures described in U.S. Pat. No. 4,267,179. The intermediates of formula (V) are prepared following procedures described in U.S. Pat. No. 4,101,666, which is incorporated herein by reference, e.g., by the acetalization of a diol of formula (VII) with a 1-(4-$C_{1-4}$alkyloxyphenyl)-2-haloethanone. In turn, the intermediates of formula (VII) can e obtained by S-alkylating an intermediate of formula (III) with (chloromethyl)oxirane and subsequent hydrolysis of the epoxide.

The previously described intermediates and starting materials may also be converted into each other following art-known functional group transformation procedures and/or particular reactive groups of said intermediates and starting materials may be selectively protected during the course of the reactions be easily removeable protective groups.

The present compounds of formula (I), the pharmaceutically acceptable acid addition salts and stereochemically isomeric forms thereof show interesting antineoplastic properties which can partly be explained by their direct antimitotic effect on dividing cells and their ability to disintegrate the normal subcellular organisation of the non dividing cells.

As generally accepted cell division, invasion and metastasis formation may be dependent upon the microtubular apparatus. At effective concentrations the present compounds interfere with the structure and function of microtubles in both interphase and mitotic cells. Microtubules are disassembled, which result in a loss of both cell polarity and the capacity of directional migration. In mitotic cells, the chromosomes are randomly dispersed within the cell, the chromatides do not separate, and cell division is arrested. In some cell lines the mitotic cells become necrotic whereas in other cell lines the process is terminated by the separate envelopment of individual chromosomes and small groups into a nuclear membrane, resulting in the formation of multinucleated cells. In vitro experiments with murine neoplasms indicate that said mitotic block and multinucleation occur with the present compounds at doses twenty fold lower than the art compound tubulozole. Further it was found that the compounds of the invention have significant anti-metastatic properties which can be demonstrated by monitering the inhibitory properties of the compounds of the invention on the spontaneous metastatic behaviour of BI6/BL6 melanoma cells [Am. J. Pathol. 97,587 (1979)].

The present compounds of formula (I) differ mainly from the prior-art compounds by their high plasma clearance and low tissue levels, combined with a marked accumulation of the compound in the tumour tissue. Due to their specific and long lasting accumulation in the tumour tissue, the present compounds of formula (I) are particularly useful for combining chemotherapy with local radiotherapy. Treatment of a tumour prior to gamma irradiation with the present compounds results in a synergistic effect upon tumour regression. In some cell lines even a striking central necrosis of the tumour was detected as a consequence of said interactive effect with irradiation.

Quite unexpectedly, similarly interactive effects were also observed when the present compounds were administered just before or even after irradiation. This unexpected effect can not solely be explained by a selective accumulation of the compound in the tumour tissue and proves the existence of an additional direct cytotoxic effect of the compound on the tumour tissue and/or an indirect interference of the compounds with the enzymatic repair mechanisms of the irradiated cells.

Consequently a more clinically relevant schedule of administration is possible due to the fact that the interactive effect with irradiation is not so strictly dependent on a rigid time interval. Though pretreatment of the present compound, preferably about 3 to 1 hour, e.g. 2 hours before irradiation, appears to give an optimal tumour regression.

Apart from the above described radiosentitizing effect some compounds of the present invention also exert a beneficial radioprotective effect on normal tissues such as, for example, the small intestine and bone marrow, and therefore limit the occurrence of acute and late side effects in critical normal tissues which are included in the irradiated volume.

The useful antineoplastic activity of the present compounds can be demonstrated in various in vitro and in vivo experiments. For example, the antineoplastic activity of the present compounds can be tested in vivo upon a number of experimental neoplasms, which are known to be predictive for antineoplastic chemotherapeutic agents such as, for example, $MO_4$ sarcoma, $L_{1210}$ leukemia, $TA_3$ carcinoma, Lewis lung 3LL tumour and pulmonary metastases, methylcholanthrene induced cacinoma, Moloney leukemia, carcinoma 180 and the like, using different treatment schedules upon different inoculation routes of the cells. The "Doubling time of $MO_4$ tumours"-test described hereinafter illustrates the striking antineoplastic properties of the present compounds and is based on the above principles.

Another important feature of the present invention is the fact that the present compounds show a low systemic toxicity, and do not induce gene mutations in the Salmonella Ames test.

In view of the useful antineoplastic properties and their low systemic toxicity the present compounds are particularly useful for the treatment of neoplastic diseases, especially when the administration of a compound of formula (I) is combined with irradiation of the neoplasm, such as gamma irradiation. It is therefore an object of the invention to provide a method for treating mammals hosting a neoplasm, said method comprises administering to said mammals an effective antineoplastic amount of a compound of formula (I) or a pharmaceutically acceptable acid addition salt thereof or stereochemically isomeric form thereof optionally in combination with irradiation of the neoplasm.

Those of skill in the pertinent art could easily determine the effective antineoplastic amount from the results presented hereinafter. In general it is contemplated that an effective amount would be from 5 mg/m$^2$ to 400 mg/m$^2$ and more preferably from 10 mg/m$^2$ to 200 mg/m$^2$ especially when the administration of the compound is combined with irradiation of the neoplasm. The effective amount of the active ingredient and appropriate amount and duration of the irradiation for the treatment of the particular neoplastic disease may depend on the species and size of the subject being treated, the particular condition and its severity, the route of administration and the formulation of the active compounds. In any case the dose to be used is one non-toxic to the host. As a dosage regimen, the amount of a compound of formula (I) and/or irradiation, should be sufficient to aid regression and palliation of the neoplastic disease in the absence of excessive deleterious side effects of a cytotoxic nature to the host harbouring the disease.

The compounds of formula (I) are most preferably applied in the form of an appropriate composition, in particularly in a composition usually employed for treatment of neoplastic diseases. To prepare the pharmaceutical compositions of this invention, an effective amount of the compound of formula (I), in acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, e.g. propyleneglycol, polyethyleneglycol, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparation which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage form for ease of administration and uniformity of dosage.

Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solution or suspensions, teaspoonfuls, tablespoonfuls and the like, and segregated multiples thereof.

Particular pharmaceutical compositions for the treatment of neoplastic diseases comprise a compound of formula (I), a pharmaceutically acceptable acid addition salt or stereochemically isomeric form thereof and a cyclodextrin or a derivative thereof. Such compositions result in a high concentration of active compound during a sufficiently long period of time in the tumour tissue without a deleterious accumulation of the compounds in the plasma or muscle tissue.

The cyclodextrin to be used in the aforementioned compositions include the pharmaceutically acceptable unsubstituted and substituted cyclodextrins known in the art more particularly $\alpha,\beta,\gamma$cyclodextrins or the pharmaceutically acceptable derivatives thereof.

Substituted cyclodextrins which can be used in the composition for use in the method of the present invention include e.g. the polyethers described in U.S. Pat. No. 3,459,731 U.S. Pat. No. 4,764,604 and EP-A-149,197 which are incorporated by reference for the definition and processes for preparation. In generally, unsubstituted cyclodextrins are reacted with an alkylene oxide, preferably under superatmospheric pressure and at an elevated temperature, in the presence of an alkaline catalyst.

Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

In the foregoing definitions the term "$C_{1-6}$alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.125 to 3, in particular 0.3 to 2, more in particular 0.3 to 1 and the MS is in the range of 0.125 to 10, in particular of 0.3 to 3 and more in particular 0.3 to 1.5.

Other references describing cyclodextrins for use in the compositions according to the present invention, and which provide a guide for the preparation and characteristics of cyclodextrins, for the process of depositing the selected agent within the cyclodextrin molecule of the use of cyclodextrins in pharmaceutical compositions include the following: "Cyclodextrin Chemistry" by M. L. Bender et al., Springer-Verlag, Berlin (1978); Advances in Carbohydrate Chemistry", Vol. 12 Ed. by M. L. Wolfrom, Academic Press, New York (157) in the chapter *The Schardinger Dextrins* by Dexter French at p. 189-260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92. p. 343–361 (1981); A. P. Croft and R. A. Bartsch in Tetrahedron, 39, p. 1417–1474 (1983); German Offenlegungsschrift DE 3118218; German Offenlegungsschrift DE 3317064; EP-A-94,157; EP-A-149,197; U.S. Pat. No. 4,659,696; and U.S. Pat. No. 4,383,992.

Of particular utility in the invention are the β-andγ-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin, hydroxypropyl γ-cyclodextrin and hydroxyethyl β-cyclodextrin, being examples. Such an alkyl ether may be a methyl ether with a degree of substitution of about 0.125 to 3, e.g. about 0.3 to 2. Such as hydroxypropyl cyclodextrin may for example be formed from the reaction between β-or γ-cyclodextrin and propylene oxide and may have a MS value of about 0.125 to 10, e.g. about 0.3 to 1.5.

In the invention, the molecules of the anti-tumour compounds of formula (I) are surrounded, at least in part, by the cyclodextrin, i.e. the agent fits into the cyclodextrin cavity.

To prepare said particular cyclodextrin based pharmaceutical compositions of the invention, the selected anti-neoplastic compounds (or compounds) of formula (I), the pharmaceutically acceptable acid addition salt or the stereochemically isomeric form thereof is deposited within the cyclodextrin molecule itself, such process being known in the art for other active agents. In the final compositions, the molar ratio of cyclodextrin-:anti-tumour compound is from about 1:1 to about 5:1, in particular, about 1:1 to about 2:1. Thus, in general, the composition will be prepared by dissolving the cyclodextrin in an aqueous solution and adding the anti-tumour compound to this solution, preferably under vigorous stirring and preferably at a temperature in the range of 10° C. to 50° C., in particular in range of 15° C. to 30° C., and preferably at room temperature.

In the final compositions, the cyclodextrin will comprise about 2.5 to 50% by weight, in particular about 2.5 to 25%, more in particular 5 to 25%, or 5 to 20%, for example about 10%, with the remainder being water, preservative, the active ingredient and any excipients.

The cyclodextrin based compositions of the invention are preferably administered orally or by parenteral injection, preferably intravenous injection. However, other modes of administration such as, rectal administration are not excluded.

For the liquid preparations of said cyclodextrin based compositions, any of the usual pharmaceutical media may be added, such as, for example, glycols, oils, alcohols and the like, however in concentrations below the level of irritation. In order to stabilize the formulations the pH may be increased or decreased or stabilized by adding appropriate acids, bases or buffer systems, e.g. citrate, phosphate buffers. Further additives may comprise substances to make the formulation isotonical, e.g. sodium chloride, mannitol, glucose and the like.

In a preferred embodiment of the invention there is provided a cyclodextrin based composition which is well suited for intravenous administration and which can be prepared very easily and quickly by simply mixing a stable and concentrated anti-neoplastic cyclodextrin composition with a normal aqueous infusion liquid such as saline, glucose solution or a mixture of saline and glucose. The concentration of the compound of formula (I) in the preferred composition for intravenous administration may vary within rather wide limits depending on the rate of infusion and the dose required by the specific circumstances. Concentration ranging from about 0.02 to about 20 mg/ml calculated on the base content, have been found adequate.

As part of the pharmaceutical composition, one may also include the same of a different active anti-neoplastic compound in a different delivery carrier so as to provide a different profile of activity, e.g. a wide range of time during which the composition shows activity or a supplement to bolster a low level at a particular point.

The following examples are intended to illustrate but not to limit the scope of the present invention, Unless otherwise stated all parts therein are by weight.

EXPERIMENTAL PART

A) Preparation of the Intermediates

Example 1 a) A mixture of 69 parts of 1,2,3-propanetriol, 142 parts of 2-bromo-1-(4-methoxyphenyl)-ethanone, 6.3 parts of 4-methylbenzenesulfonic acid, 80 parts of 1-butanol and 450 parts of benzene was stirred and refluxed for 20 hours with water separator. The reaction mixture was cooled and poured into a diluted sodium hydroxide solution. The layers were separated and the aqueous phase was extracted twice with methylbenzene. The combined organic phases were washed with water, dried, filtered and evaporated, yielding 186.5 parts of 2-(bromomethyl)-2-(4-methoxyphenyl)-1,3-dioxolane-4-methanol as a residue (interm. 1).

b) A solution of 185 parts of 2-(bromomethyl)-2-(4-methoxyphenyl)-1,3-dioxolane-4-methanol in 114 parts of pyridine and 900 parts of trichloromethane was stirred and cooled to 5° C. Then there were also added dropwise 118 parts of benzoyl chloride (exothermic reaction, the temperature roses to about 15° C.). Upon complete addition, stirring was continued first for one hour while cooling in an ice-bath and further for 2 hours at room temperature. The reaction mixture was poured into water and the layers were separated. The aqueous phase was extracted with trichloromethane. The combined organic phases were washed twice with water, dried, filtered and evaporated. The residue was crystallized from methanol, yielding 217 parts of cis-[2-(bromomethyl)-2-(4-methyoxyphenyl)-1,3-dioxolan-4-ylmethyl] benzoate (interm. 2).

c) To a stirred and refluxed (15 minutes) mixture of 51.7 parts of 1H-imidazole and 136.8 parts of a sodium methanolate solution 30% were added 150 parts of N,N-dimethylformamide. The methanol was distilled off and a solution of 206 parts of cis-[2-(bromomethyl)-2-(4-methoxyphenyl)-1,3-dioxolan-4-ylmethyl] benzoate in 450 parts of N,N-dimethylformamide was added dropwise during 20 minutes. Upon complete addition, stirring was continued for 3 hours at reflux. After cooling, 1800 parts of water were added and the layers were separated. The aqueous layer and the organic layer were extracted, washed with water, dried and evaporated. The residues were combined and purified to yield cis-2-(1H-imidazol-1-ylmethyl)-2-(4-methoxyphenyl)-1,3-dioxolane-4-methanol (interm. 3).

d) To a stirred mixture of 12 parts of cis-2-(1H-imidazol-1-ylmethyl)-2-(4-methoxyphenyl)-1,3 -dioxolane-4-methanol and 70 parts of pyridine were added dropwise 6.4 parts of methanesulfonyl chloride (exothermic reaction). After the addition of 70 parts of pyridine, the whole was stirred for 3 hours at room temperature. The reaction mixture was poured into water. The precipitated product was filtered off and crystallized from benzene, yielding 6.4 parts of cis-2-(1H-imidazol-1-ylmethyl)-2-(4-methoxyphenyl)-1,3-dioxolane-4-methanol methanesulfonate(ester) (interm. 4).

Example 2 a) A mixture of 53 parts of 1-(4-ethoxyphenyl)-2-(1H-imidazol-1-yl)ethanone monohydrochloride, 100 parts of 1,2,3-propanetriol, 45 parts of 4-methylbenzenesulfonic acid and 270 parts of methylbenzene was stirred overnight at reflux temperature using a water separator. After cooling, the reaction mixture was poured into a sodium hydrogen carbonate solution and the product was extracted with trichloromethane. The extract was washed with water, dried, filtered and evaporated, yielding 57.5 parts (94.4%) of (cis+trans)-2-(4-ethoxyphenyl)-2-(1H-imidazol-1-ylmethyl)-1,3-dioxolane-4-methanol as a residue (interm. 5).

b) A mixture of 45 parts of 2-naphthalenesulfonyl chloride, 57 parts of (cis+trans)-2-(4-ethoxyphenyl)-2-(1H-imidazol-1-ylmethyl)-1,3-dioxolane-4-methanol, 70 parts of N,N-diethylethanamine and 260 parts of dichloromethane was stirred overnight at room temperature. The reaction mixture was poured into water and the product was extracted with dichloromethane. The extract was washed with water, dried, filtered and evaporated. The residue was purified by column chromatography over silica gel using a mixture of trichloromethane and methanol (99.1 by volume) as eluent. The first fraction was collected and the eluent was evaporated, yielding 24.4 parts (27.4%) of cis-[[2-(4-ethoxyphenyl)-2-(1H-imidazol-1-ylmethyl)-1,3-dioxolan-4-yl]methyl]-2-naphthalenesulfonate as a residue (interm. 6).

In a similar manner there were also prepared:
cis-[[2-(1H-imidazol-1-ylmethyl)-2-(4-propoxyphenyl)-1,3-dioxolan-4-yl]methyl]-2-naphthalenesulfonate(ester) as a residue (interm. 7); and
cis-]]2-(1H-imidazol-1-ylmethyl)-2-[4-(1-methylethoxy)phenyl]-1,3-dioxolan-4 -yl]methyl]-2-naphthalenesulfonate(ester) as a residue (interm. 8).

Example 3 a) A mixture of 53 parts of 2-naphthalenesulfonyl chloride, 30 parts of (S)-2,2-dimethyl-1,3-dioxolane-4-methanol, 70 parts of N,N-diethylethanamine and 180 parts of ethyl acetate was stirred for 2 hours at room temperature. The reaction mixture was poured into water and the product was extracted with methylbenzene. The extract was washed with water, dried, filtered and evaporated. The residue was purified by column chromotography over silica gel using trichloromethane as eluent. The pure fractions were collected and the eluent was evaporated, yielding 62.8 parts (85.8%) of (R)-[(2,2-dimethyl-1,3-dioxolan-4-yl)methyl]2-naphthalenesulfonate (interm. 9).

b) A mixture of 62 parts of (R)-[(2,2-dimethyl-1,3-dioxolan-4-yl)methyl]2-naphthalenesulfonate, 400 parts of a hydrochloric acid solution 10% and 320 parts of 2-propanone was stirred for 2 hours at reflux temperature. After evaporation, the residue was taken up in trichloromethane. The organic layer was washed with water, dried, filtered and evaporated. The residue was purified by column chromatography over silica gel using a mixture of trichloromethane and methanol (98.2 by volume) as eluent. The pure fractions were collected and the eluent was evaporated, yielding 40 parts (73.7%) of (R)-(2,3-dihydroxypropyl) 2-naphthalenesulfonate as a residue (interm. 10).

c) A mixture of 35 parts of (R)-(2,3-dihydroxypropyl) 2-naphthalenesulfonate, 21.6 parts of 2-(1H-imidazol-1-yl)-2-(4-methoxyphenyl)ethanone, 39 parts of 4-methylbenzenesulfonic acid and 720 parts of methylbenzene was stirred overnight at reflux temperature using a water separator. After cooling, the reaction mixture was poured into a sodium hydrogen carbonate solution. The separated organic layer was washed with water, dried, filtered and evaporated. The residue was purified by column chromatography over silica gel using a mixture of trichloromethane, ethyl acetate and hexane (50:30:20 by volume) as eluent. The pure fractions were collected and the eluent was evaporated. The residue was triturated in 1,1'-oxybisethane. The product was filtered off and dried, yielding 11.1 parts (23.0%) of (2R,cis)-[[2-(1H-imidazol-1-ylmethyl)-2-(4-methoxyphenyl)-1,3-dioxolan -4-yl]methyl]2-naphthalenesulfonate (interm. 11).

In a similar manner there were also prepared:
(2R,trans)-[[2-(1H-imidazol-1-ylmethyl)-2-(4-methoxyphenyl)-1,3-dioxolan-4-yl]methyl]2-naphthalenesulfonate (interm. 12);
(2S,cis)-[[2-(1H-imidazol-1-ylmethyl)-2-(4-methoxyphenyl)-1,3-dioxolan-4-yl]methyl]2-naphthalenesulfonate (interm. 13); and
(2S,trans)-[[2-(1H-imidazol-1-ylmethyl)-2-(4-methoxyphenyl)-1,3-dioxolan-4-yl]methyl]2-naphthalenesulfonate (interm. 14).

B) Preparation of Final Compounds

Example 4

A mixture of 2.4 parts of ethyl (4-mercaptophenyl)carbamate, 3.5 parts of cis-2-(1H-imidazol-1-ylmethyl)-2-(4-methoxyphenyl)-1,3-dioxolan-4-methanol methanesulfonate(ester), 1.7 parts potassium carbonate and 120 parts of 2-propanone was stirred and refluxed overnight under nitrogen atmosphere. Stirring was continued over week-end at room temperature. The reaction mixture was poured into water and the product was extracted with trichloromethane. The extract was washed with water, dried, filtered and evaporated. The residue was purified by column chromatography over silica gel using a mixture of trichloromethane and methanol (98.2 by volume) as eluent. The pure fractions were collected and the eluent was evaporated. The residue was triturated in 2,2'-oxybispropane. The product was filtered off and dried, yielding 4.3 parts of ethyl cis-[4-[[[2-(1H-imidazol-1-ylmethyl)-2-(4-methoxyphenyl)-1,3-dioxolan-4-yl]methyl]thio]phenyl]carbamate; mp. 137° C. (compound 1).

In a similar manner there were also prepared:
ethyl cis-[4-[[[2-(4-ethoxyphenyl-2-(1H-imidazol-1-ylmethyl)-1,3-dioxolan-4-yl]methyl]thio]phenyl]carbamate;; mp. 141.4° C.(compound 2);
(+)-ethyl (2R,cis)-[4-[[[2-(1H-imidazol-1-ylmethyl)-2-(4-methoxyphenyl)-1,3-dioxolan-4-yl]methyl]thio]phenyl]carbamate; mp. 103.0° C.,$[\alpha]_D$= +8.85°(c=1% in methanol) (compound 3);
(+)-ethyl (2R,trans)-[4-[[[2-(1H-imidazol-1-ylmethyl)-2-(4-methoxyphenyl)-1,3-dioxolan-4-yl]methyl]thio]phenyl]carbamate; mp. 106.8° C.,$[\alpha]_D$= +4.62°(c=1% in methanol) (compound 4);

(−)-ethyl (2S,cis)-4-[[[2-(1H-imidazol-1-ylmethyl)-2-(4-methoxyphenyl)-1,3-dioxolan-4-yl]methyl]thio]-phenyl]carbamate; mp. 102.2° C.,$[\alpha]_D = -9.09°$(c=1% in methanol) (compound 5);
(−)-ethyl (2S,trans)-[4-[[[2-(1H-imidazol-1-ylmethyl)-2-(4-methoxyphenyl)-1,3-dioxolan-4-yl]methyl]thio]-phenyl]carbamate; mp. 106.8° C.,$[\alpha]_D = -5.06°$(c=1% in methanol) (compound 6);
ethyl cis-[4-[[[2-(1H-imidazol-1-ylmethyl)-2-[4-(1-methylethoxy)phenyl]-1,3-dioxolan-4-yl]methyl]thio]phenyl]carbamate; mp. 192.2° C.(compound 7); and
ethyl cis-[4-[[[2-(1H-imidazol-1-ylmethyl)-2-(4-propoxyphenyl)-1,3-dioxolan-4-yl]-methyl]thio]phenyl]carbamate; mp. 129.5° C.(compound 8).

Composition Examples

The following formulations exemplify typical compositions in dosage unit form suitable for systemic administration to animal and human subjects in accordance with the present invention "Active ingredient"(A.I.) as used throughout these examples.

Example 5: Oral Drops 500 g of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 0.01 g of the A.I. per ml. The resulting solution was filled into suitable containers.

Example 6: Oral Solution 9 g of methyl 4-hydroxybenzoate and 1 part of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l, 1,2,3-propanetriol and 3 l of sorbitol 70% solution were added thereto. 40 g of sodium saccharin were dissolved in 0.5 l of water and 2 ml of rasberry and 2 ml of gooseberry essence were added. The latter solution was combined with the former, water was added q.s. to a volume of 20 l providing an oral solution comprising 0.005 g of the A.I. per teaspoonful (5 ml). The resulting solution was filled in suitable containers.

Example 7: Capsules 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 0.02 g of the A.I.

Example 8: Film-Coated Tablets

Preparation of tablet core

A mixture of 100 g of the A.I., 570 g lactose and 200 g starch was mixed well and thereafter humidified with a solution of 5 g sodium sulfate and 10 g polyvinylpyrrolidone (Kollidon-K 90 ®) in about 200 ml of water. The wet powder mixture was sieved, dried and sieved again. Then there was added 100 g microcrystalline cellulose (Acivel ®) and 15 g hydrogenated vegetable oil (Sterotex ®). The whole was mixed well and compressed into tablets, giving 10,000 tablets, each comprising 0.01 g of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109 ®) and the whole was homogenated. The tablet cores were coated with the thus obtained mixture in a coating apparatus.

Example 9: Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 0.004 g A.I. per ml. The solution was sterilized by filtration U.S.P. XVII p. 811) and filled in sterile containers.

Example 10: Suppositories 3 g. A.I. was dissolved in a solution of 3 g 2,3-dihydroxy-butanedioic acid in 25 ml polyethylene glycol 400. 12 G surfactant (SPAN ®) and triglycerides (Witepsol 555 ®) q.s. ad 300 g were molten together. The latter mixture was mixed well with the former solution. The thus obtained mixture was poured into moulds at a temperature of 37~38° C. to form 100 suppositories each containing 0.03 g of the active ingredient.

Example 11: Cyclodextrin Based Solutions a) to 70 ml of an isotonic solution was added 10 g hydroxypropyl-β-cyclodextrin (MS=0.43) and 1 g of the A.I., in particular ethyl cis-[4-[[[2-(1H-imidazol-1-ylmethyl) -2-(4-methoxyphenyl)-1,3-dioxolan-4-yl]methyl]thio]phenyl]carbamate. After stirring for 10 minutes at room temperature the solution was supplemented with water for injection. The solution was sterilized and filled in containers.

b) To 80 ml of a physiological sodium chloride solution is added 15 g hydroxyethyl-β-cyclodextrin (MS=0.98) and 1 g of the A.I. The mixture is warmed (45–50° C.) and stirred well and made up to 10 ml by addition of water for injection. The solution was sterilized and filled into ampules.

c) 5 g hydroxyethyl-γ-cyclodextrin (MS=0.77) and 0.5 g A.I. is dissolved in 100 ml of a physiological sodium chloride solution at 30° C. and filtered through a membrane filter (0.45 microns). The solution was filled into ampules and sterilized.

D) Pharmacological Examples

Example 12: Determination of Plasma and Tissue Levels in CDF₁ Mice

The compound concentrations in pooled plasma and MO₄ tumour tissue were determined after oral treatment with 80 mg/kg of ethyl cis-[4-[[2-(1H-imidazol-1-ylmethyl)-2-(4-methoxyphenyl)-1,3,-dioxolan-4-yl]methylthio]phenyl]carbamate (compound no. 1) and 160 mg/kg of the prior art compound ethyl cis-[4-[[2-(2,4-dichlorophenyl)-2-(1H-imidazol-1-ylmethyl)-1,3-dioxolan-4-yl]methylthio]phenyl]carbamate monohydrochloride.monohydrate. The said prior-art compound was described in U.S. Pat. No. 4,490,540 and is generically designated as tubulozole. In tables 1 and 2 there are depicted the plasma concentrations in μg/ml and tumour concentrations in μg/g, 1 and 24 hours after oral treatment with the test compound.

TABLE 1

Compound No. 1 plasma and tumour levels in mice after oral (80 mg/kg) administration

| | Plasma conc. in μg/ml | Tumour conc. in μg/g |
|---|---|---|
| 1 hour | 4.8 | 7.9 |
| 24 hours | 0.08 | 1.3 |

TABLE 2

Tubulozole plasma and tumour levels in mice after oral (160 mg/kg) administration.

| | Plasma conc. in μg/ml | Tumour conc in μg/g |
|---|---|---|
| 1 hour | 20.8 | 5.1 |
| 24 hours | 0.9 | 0.5 |

Conclusion:

In comparison with prior-art compound tubulozole the compound of the present invention, comp. No. 1, appeared to give lower plasma levels and the accumulate more selectively in the tumour tissue. After 1 hour, the compound of the present invention showed a marked intratumoural accumulation and a sufficiently effective compound level was maintained till 24 hours after oral administration (1.3 μg/g).

Example 13: Doubling Time (In Days) of MO₄ Tumours

Tumour and animals

MO₄ cells are maintained in vitro in tissue culture flasks in supplemented EMEM culture medium and held in a humidified atmosphere of 5% CO₂ in air at 37° C. 10⁶ MO₄ cells were injected subcutaneously into the left inguinal region of syngeneic CDF₁ mice resulting in subcutaneous tumours with reproducible growth.

Evaluation of tumour growth

Measurable tumours approximating 1 cm³ were obtained 14 days after injection. The first measurement (obtained by multiplying the square of the smallest diameter with the largest diameter) was designated as the initial tumour volume at 'day zero' (TVo). Individual tumours were measured on consecutive days and the relative tumour growth was denominated as a percentage of the initial tumour volume. The tumour doubling time (Td) was defined as the time to double the initial tumour volume (Td=2TVo/TVox100%=200%). Individual Td's were estimated by linear interpolation on the plots of log tumour volume versus day of measurement. When no doubling of the tumour volume was achieved, the last day of observation was taken as a lower limit of the actual Td ('censored Td') and further analyzed using 'survival analysis methods'. This consisted of comparing the treated groups with their corresponding controls using the Peto-Peto-Wilcoxon test. Due to the 'censored' nature of the data, results were reported as median values.

Irradiation

Animals were synthesized with a 0.2 ml intraperitoneal injection of a 2.5% aqueous solution of 2,2,2-tribromoethanol (Janssen Chimica, Beerse, Belgium). At day zero, tumours were locally irradiated with collimated gamma-irradiation from ⁶⁰Co source. The dose rate was 52.7 Gy per hour.

Drug

All concentrations of ethyl cis-[4-[[2-(1H-imidazol-1-ylmethyl)-2-(4-methoxyphenyl)-1,3-dioxolan-4-yl]methylthio]phenyl]carbamate were formulated in a hydroxypropyl-β-cyclodextrin (MS=0.43) 10% solution and administered by oral gavage.

Results

One single dose of 5. 10, 20 or 40 mg/kg cis-[4-[[2-(1H-imidazol-1-ylmethyl)-2-(4-methoxyphenyl)-1,3-dioxolan-4-yl]methylthio]phenyl]carbamate or a placebo was given by oral gavage at 'day zero' 2 hours before 10 Gy radiation. The observed tumour doubling times (Td) for the various doses are gathered in table 3.

TABLE 3

Tumour doubling times after oral treatment of compound No. 1, two hours before 10 Gy radiation.

| | 0 mg/kg | 5 mg/kg | 10 mg/kg | 20 mg/kg | 40 mg/kg |
|---|---|---|---|---|---|
| Tumour doubling time in days | 5 | 10.5 | 12.5 | 11.5 | 10.5 |

We claim:

1. A chemical compound having the formula

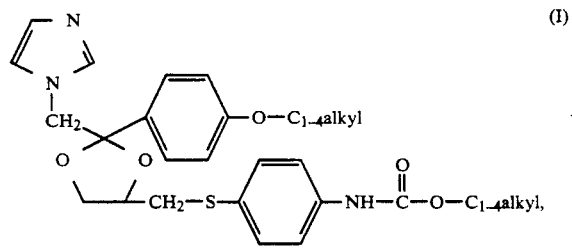

an acid addition salt or sterochemically isomeric form thereof.

2. A chemical compound according to claim 1 wherein the substituents on the dioxolane moiety of formula (I) have a cis configuration.

3. A chemical compound according to claim 1 wherein the compound is ethyl cis-[4-[[2-(1H-imidazol-1-ylmethyl)-2-(4-methoxyphenyl)1,3-dioxolan-4-yl]methylthio]phenyl]carbamate or a pharmaceutically acceptable acid addition salt thereof.

4. A pharmaceutical composition comprising an inert carrier, and, if desired, other additives, and as active ingredient an effective antineoplastic amount of a chemical compound of formula (I) as claimed in claim 1, said effective antineoplastic amount being an amount effective to treat a carcinoma, sarcoma or leukemia neoplasm.

5. A pharmaceutical composition according to claim 4 wherein the substituents on the dioxolane moiety of formula (I) have a cis configuration.

6. A pharmaceutical composition according to claim 4 wherein the compound is ethyl cis-[4-[[2-(1H-imidazol-1-ylmethyl)-2-(4-methoxyphenyl)-1,3-dioxolan-4-yl]methylthio]phenyl]carbamate or a pharmaceutically acceptable acid addition salt thereof.

7. A pharmaceutical composition according to claim 4 which comprises a cyclodextrin.

8. A pharmaceutical composition according to claim 7 wherein said cyclodextrin is a $\beta$- or $\gamma$- cyclodextrin or a pharmaceutically acceptable derivative thereof.

9. A pharmaceutical composition according to claim 8 wherein the cyclodextrin is a $\beta$- or $\gamma$-cyclodextrin ether or mixed ether wherein the ether substituents are $C_{1-6}$alkyl, hydroxy$C_{1-6}$alkyl, carboxy$C_{1-6}$alkyl or ($C_{1-6}$alkyloxycarbonyl)$C_{1-6}$alkyl.

10. A composition according to claim 7, wherein the molar ratio of cyclodextrin: compound of formula (I) in said pharmaceutical composition is from about 1:1 to about 5:1.

11. A composition according to claim 7, wherein said cyclodextrin is present in said pharmaceutical composition in an amount of about 5 to 25% weight percent.

12. A composition according to claim 7, which is applicable for intravenous application.

13. A method of treating a carcinoma, sarcoma or leukemia neoplasm in a mammal, which comprises administering to said mammal, an effective antineoplastic amount of a chemical compound of formula (I) as claimed in claim 1, said effective antineoplastic amount being an amount effective to treat a carcinoma, sarcoma or leukemia neoplasm.

14. A method according to claim 13, wherein the substituents on the dioxolane moiety of formula (I) have a cis configuration.

15. A method according to claim 13, wherein the compound is ethyl cis-[4-[[2-(1H-imidazol-1-ylmethyl)-2-(4-methoxyphenyl)-1,3-dioxolan-4-yl]methylthio]phenyl]carbamate or a pharmaceutically acceptable acid addition salt thereof.

16. A method according to claim 13, whereby the neoplasm is irradiated before or after the administration of the chemical compound of formula (I).

17. A method of treating a carcinoma, sarcoma or leukemia neoplasm in a mammal, which comprises administering to said mammal a pharmaceutical composition as claimed in claim 7.

18. A method according to claim 17, whereby the neoplasm is irradiated before or after the administration of the active ingredient.

* * * * *